(12) United States Patent
Abu Bakar et al.

(10) Patent No.: US 8,722,099 B2
(45) Date of Patent: May 13, 2014

(54) POROUS BIOCERAMIC COMPOSITION FOR BONE REPAIR

(71) Applicant: Universiti Putra Malaysia, Selangor (MY)

(72) Inventors: Md Zuki Abu Bakar, Serdang (MY); Bahaa Fakri Hussein, Serdang (MY); Noordin Mohamed Mustapha, Serdang (MY); Norimah Yusof, Serdang (MY); Elias Saion, Serdang (MY)

(73) Assignee: Universiti Putra Malaysia, Selangor (MY)

( * ) Notice: Subject to any disclaimer, the term of this patent is extended or adjusted under 35 U.S.C. 154(b) by 0 days.

(21) Appl. No.: 14/040,632

(22) Filed: Sep. 28, 2013

(65) Prior Publication Data

US 2014/0027939 A1 Jan. 30, 2014

Related U.S. Application Data

(63) Continuation of application No. 13/143,343, filed as application No. PCT/MY2009/000069 on Jun. 9, 2009, now Pat. No. 8,545,894.

(30) Foreign Application Priority Data

Jan. 2, 2009 (MY) ................ PI20090002

(51) Int. Cl.
*A61K 35/56* (2006.01)

(52) U.S. Cl.
USPC .......................................... 424/547

(58) Field of Classification Search
USPC .......................................... 424/547
See application file for complete search history.

(56) References Cited

U.S. PATENT DOCUMENTS

2005/0118230 A1   6/2005   Hill et al.

FOREIGN PATENT DOCUMENTS

| EP | 1 270 025 A2 | 1/2003 |
|---|---|---|
| EP | 1 712 244 A1 | 10/2006 |
| WO | WO 94/17838 A1 | 8/1994 |

OTHER PUBLICATIONS

Zuki et al., "Mineral Composition of the Cockle (*Andara granosa*) Shells, Hard Clamp (*Meretrix meretrix*) Shells and Corals (*Porites* spp.): A Comparative Study", Journal of Animal and Veterinary Advances, 3 (7):445-447 (2004).
Hulbert et al., "Potential of Ceramic Materials as Permanently Implantable Skeletal Prostheses", J. Biomed. Mater. Res., 4: 433-456 (1970).
Nagata and Saito, "Effects of simultaneous intakes of indigestible dextrin and diacylglycerol on lipid profiles in rats fed cholesterol diets", Nutrition, 22: 395-400 (2006).
Demers et al., "Natural coral exoskeleton as a bone graft substitute: A review", Bio-Med. Mater. & Eng., 12:15-35 (2002).
Vuola et al., "Bone marrow induced osteogenesis in hydroxyapatite and calcium carbonate implants", Biomaterials, 17: 1761-1766 (1996).
Islam et al., "Characterization of calcium carbonate and its polymorphs from cockle shells (*Anadara granosa*)", Powder Technology, 213: 188-191 (2011).

*Primary Examiner* — Karen Cochrane Carlson
*Assistant Examiner* — Natalie Moss
(74) *Attorney, Agent, or Firm* — Steven M. War, Esq.

(57) ABSTRACT

The present invention relates to a porous bioceramic composition for bone repair and method of fabrication of the same. 3D-scaffolds were fabricated with a novel micro- and macro-architecture. Porous scaffolds based on dextrin, dextran, gelatin and biomineral ($CaCO_3$) powder were fabricated by heating and freeze-drying methods. Fabrication of different compositions of porous scaffolds (20, 30 wt % of gelatin, 20, 40 wt % dextrin, 30, 40, 50, 60 wt % dextran bounder with the constant quantity of $CaCO_3$ 50 g). The scaffolds properties were characterized by x-ray diffraction (XRD), differential scanning calorimetry (DSC), scanning electron microscopy (SEM) and compression tests.

13 Claims, 24 Drawing Sheets

POROUS BIOCERAMIC COMPOSITION FOR BONE REPAIR

CROSS-REFERENCE TO RELATED APPLICATION

This application is a continuation of U.S. application Ser. No. 13/143,343 filed Jul. 5, 2011.

TECHNICAL FIELD OF INVENTION

The present invention relates to a porous composition for bone scaffold, and more particularly, to a porous composition for bone scaffold having excellent biocompatibility, bioaffinity and bioactivity with good mechanical properties.

BACKGROUND OF INVENTION

Tissue or organ repair has been the ultimate goal of surgery from ancient times to the present day. Biomaterials, as the structural components of medical devices, are used extensively in the treatment of disease, trauma and disability. The most significant advances have been made through the development of so-called bioactive materials. These bioactive materials interact with the host tissues to assist and improve the healing process. $CaCO_3$ has been used for bone repair in the form of ceramic blocks, granules or $CaCO_3$ cement, it is a weak bioceramic alone without dextrin, gelatin, dextran and thus cannot be used on its own as major load-bearing implants in the human body. Dextrin was used because it is very firm, rigid and it is more tacky and faster setting. The process to produce the scaffolds is simple without using any sophisticated equipment and the scaffolds can be ready within 4-5 days. Easily sterilized either by exposure to high temperatures or gamma radiation and remain unaffected by one of these techniques. This scaffolds fall into the III category of medical devices, which are medical devices meant for permanent use which are not directly in contact with the blood stream nor the central nervous system, but do exert a biological effect or are absorbed totally or partially.

One of the most widely studied hard tissue engineering approaches seeks to regenerate the lost or damaged tissue by making use of the interactions between cells and biodegradable scaffolds. This strategy usually involves the seeding and in vitro culturing of cells within a 3-D polymeric matrix—a scaffold—prior to implantation. The bioresorbable scaffold must be biocompatible and porous interconnected network to facilitate rapid vascularization and growth of newly formed tissue.

Various source of Calcium Carbonate were used previously, some of the sources are limestone, coral which are found in a balance ecosystem. Natural coral exoskeleton derived from marine reefs is composed of calcium carbonate. It was introduced as a substitute for bone-graft in the mid-1970s, and has been used clinically to treat a variety of orthopedic and craniofacial defects of bone. This type of coral besides their endangered species is very nature expensive, and sometimes very expensive to collect. Limestone is a rock collects from the deep-seabed different from the coral as a biominerals. These materials are well known for their excellent bone-bonding capabilities but they are brittle and have poor resistance to compressive stress. In order to minimize the dependency of the above sources, the cockle shell which is easily available is used. The present invention of porous bioceramic composition has excellent bone bonding capabilities, tough and good resistance to compressive stress.

Calcium carbonate-based ceramic in combination with dextrin were used as a novel technology in this study. Gelatin and dextran are another two materials in this component to support the scaffolds.

The porous 3-D scaffolds prepared contain mainly cockle shells ($CaCO_3$) and dextrin, and process through the heating and freeze-drying methods.

SUMMARY OF THE INVENTION

It is an object of the present invention to provide a porous composition for bone scaffold having high mechanical properties.

It is another object of the present invention to provide a porous composition for bone scaffold having proper size of pores and porosity as well as applicable mechanical properties in human body to promote fast tissue reaction and osteointegration due to its large specific surface area.

It is still another object of the present invention to provide a porous composition for bone scaffold without any problems due to the thermal difference.

It is still another object of the present invention to provide a porous composition for bone scaffold which can control its dissolution rate and biological properties in human body.

It is still another object of the present invention to provide a method for manufacturing the same. According to the method of the present invention, the porosity of the porous composition substrate can be adjusted appropriately.

In order to achieve these and other objects, the present invention provides a porous composition for bone scaffold. The porous composition according to the present invention comprising a mixture of cockle shell powder, dextrin, gelatin and dextran.

Wherein it is preferable that the average size of pores in the porous composition substrate is also between 20-400 nm.

The present invention also provides to a method for preparing a porous composition for bone scaffold. The method of the present invention comprises the steps of: (a) dissolving gelatin, dextran and dextrin in hot deionized water, (b) stirring the mixture, (c) adding cockle shell powder to the mixture, (d) pouring the mixture into a shaped wax block, (e) drying the mixture in room temperature, f) removing the shaped wax block and obtaining a scaffold.

The present invention also provides another method for preparing a porous composition for bone scaffold. The method of the present invention comprises the steps of: a) dissolving gelatin, dextran and dextrin in hot deionized water, and adding cockle shell powder to the mixture (b) stirring the mixture, (c) pouring the mixture into a shaped wax block, (d) drying the mixture in a freeze drying machine.

DETAILED DESCRIPTION OF THE PREFERRED EMBODIMENT

Figure 1A:
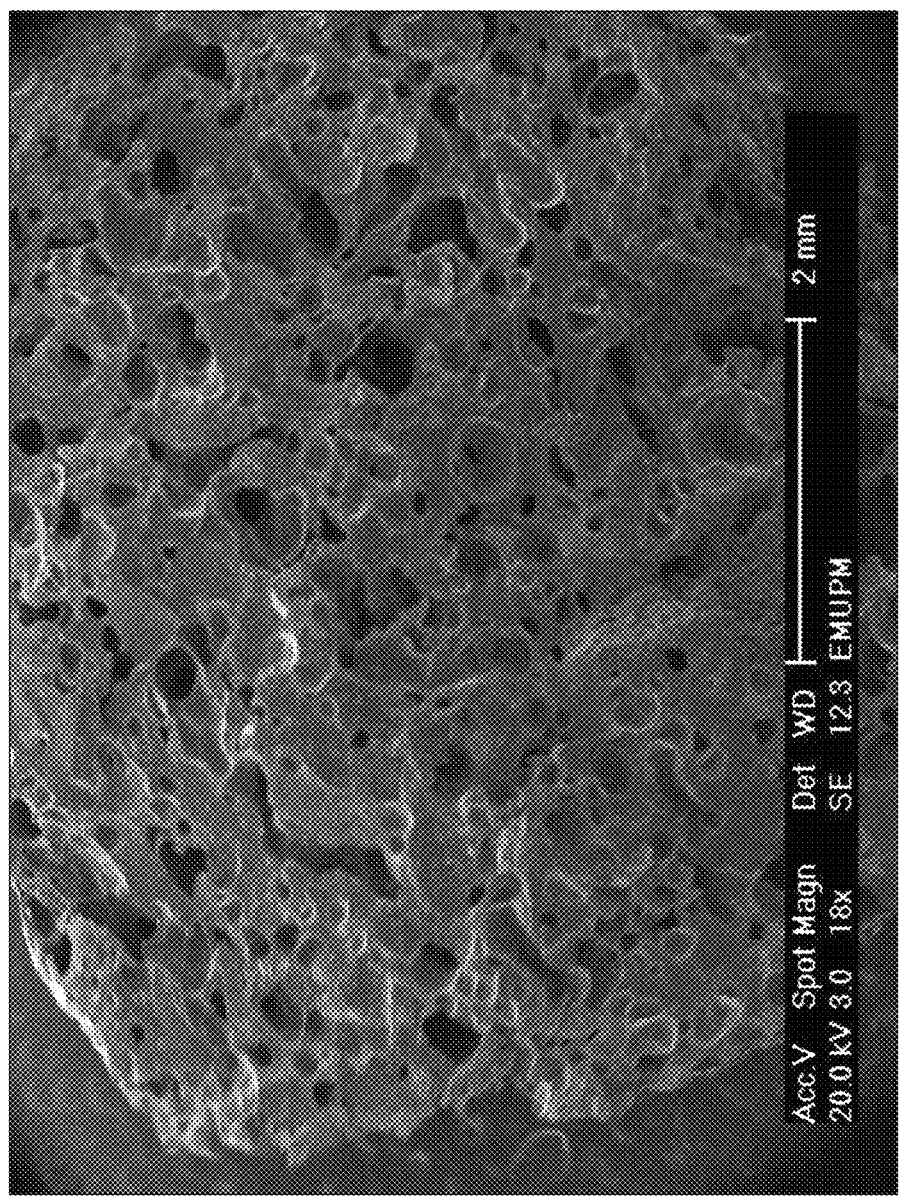
FIGS. 1A-C illustrate the scaffold contained of macro-micropores with different sizes and a uniform interior of sample 334.
Figure 1B:
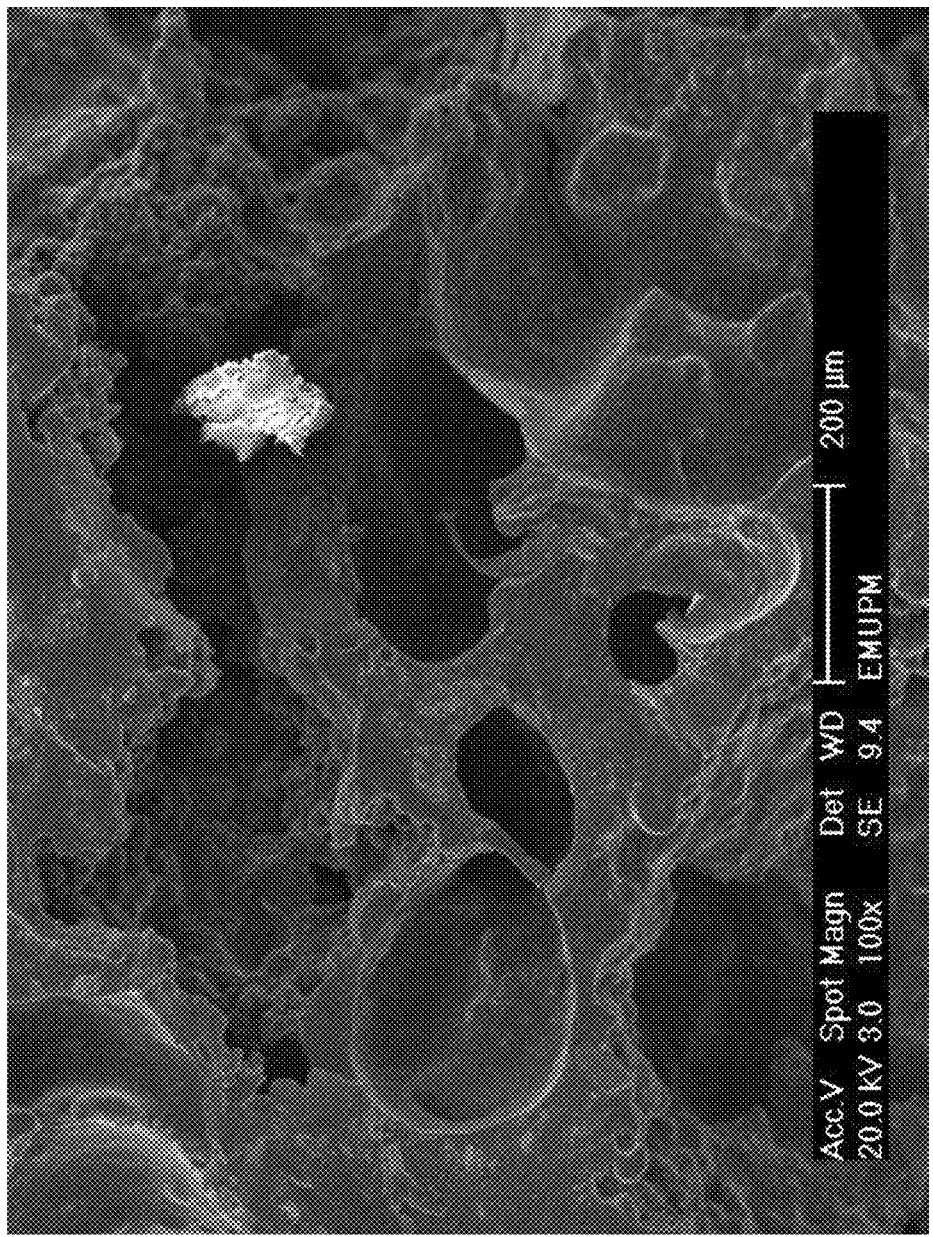
Figure 1C:
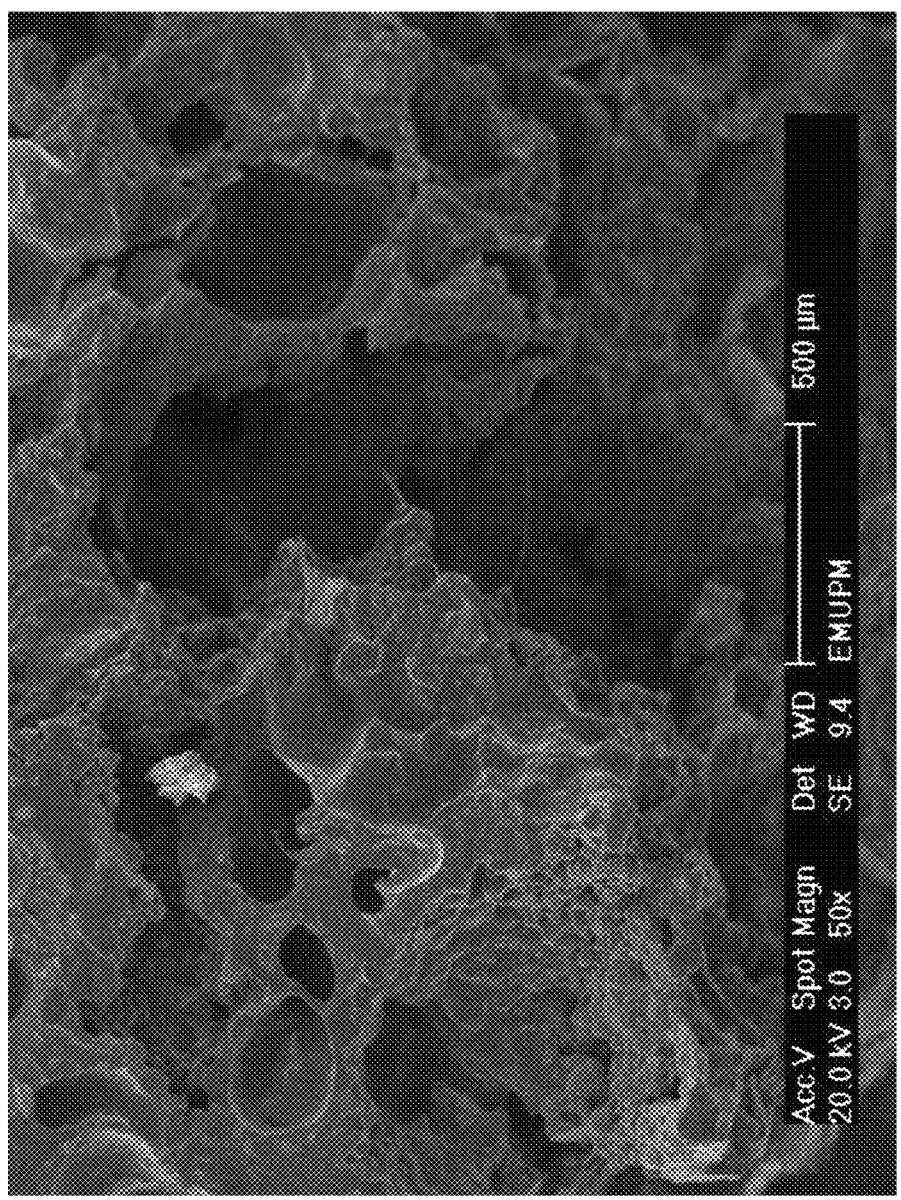
Figure 2A:
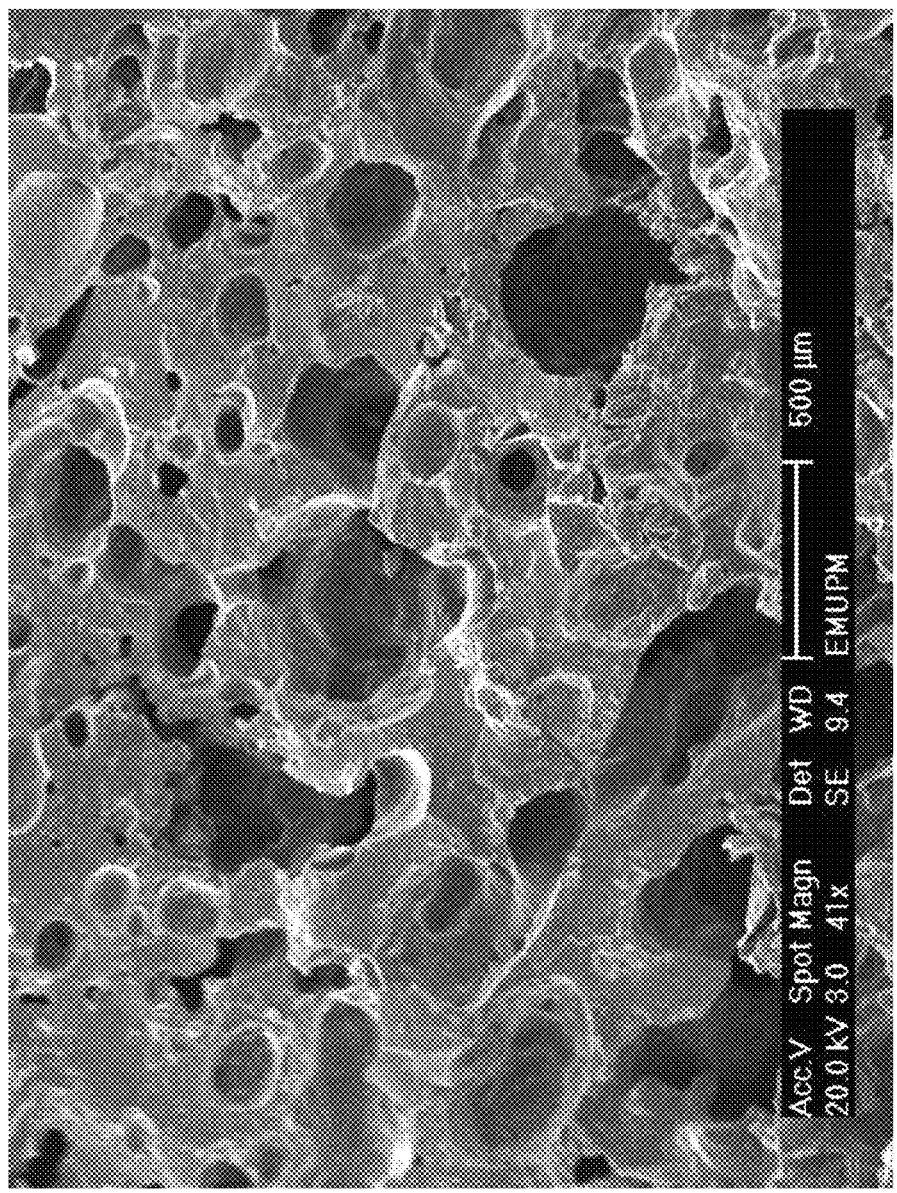
FIGS. 2A-D illustrates the scaffold contained of macro-micropores with different sizes and a uniform interior of sample 334.
Figure 2B:
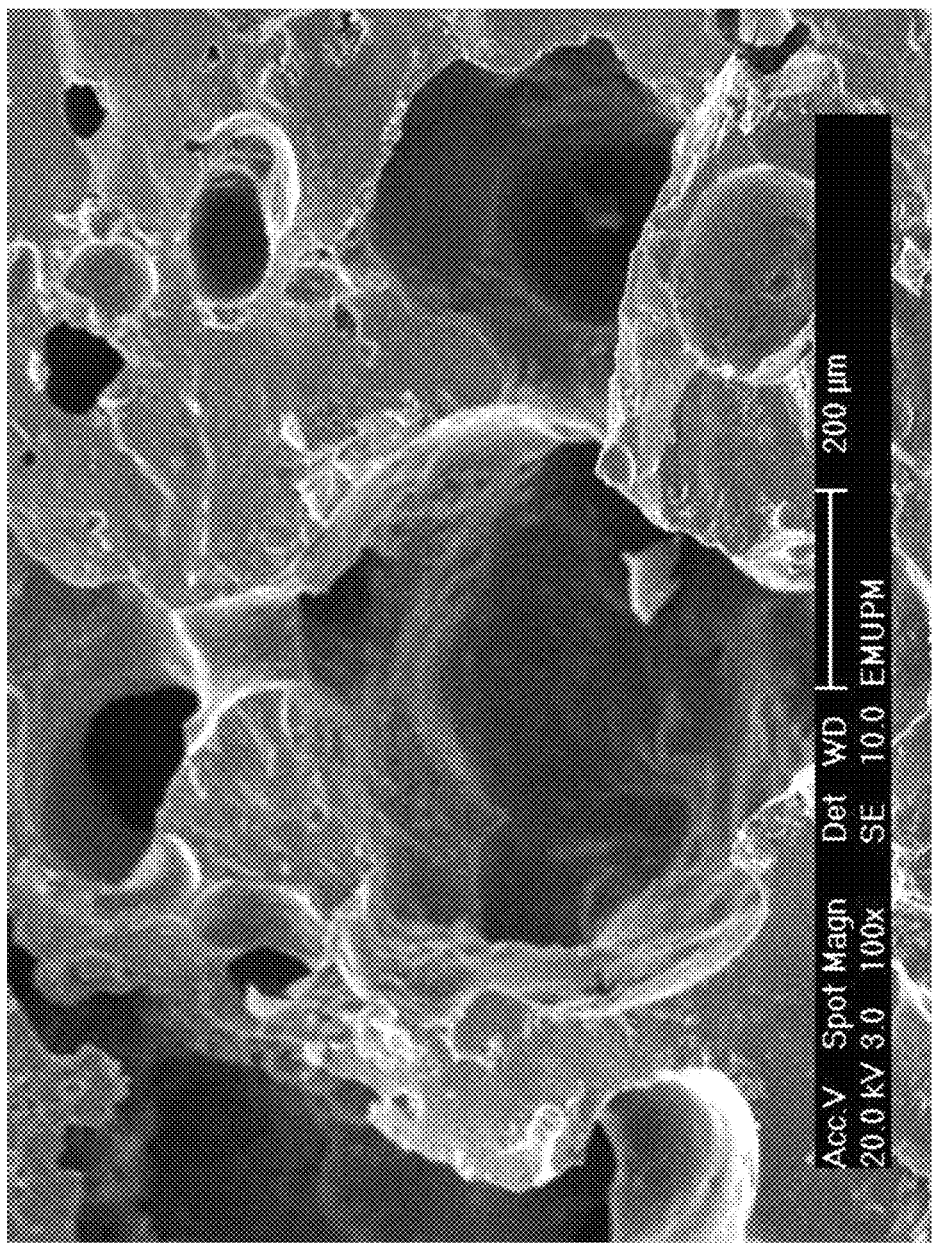
Figure 2C:
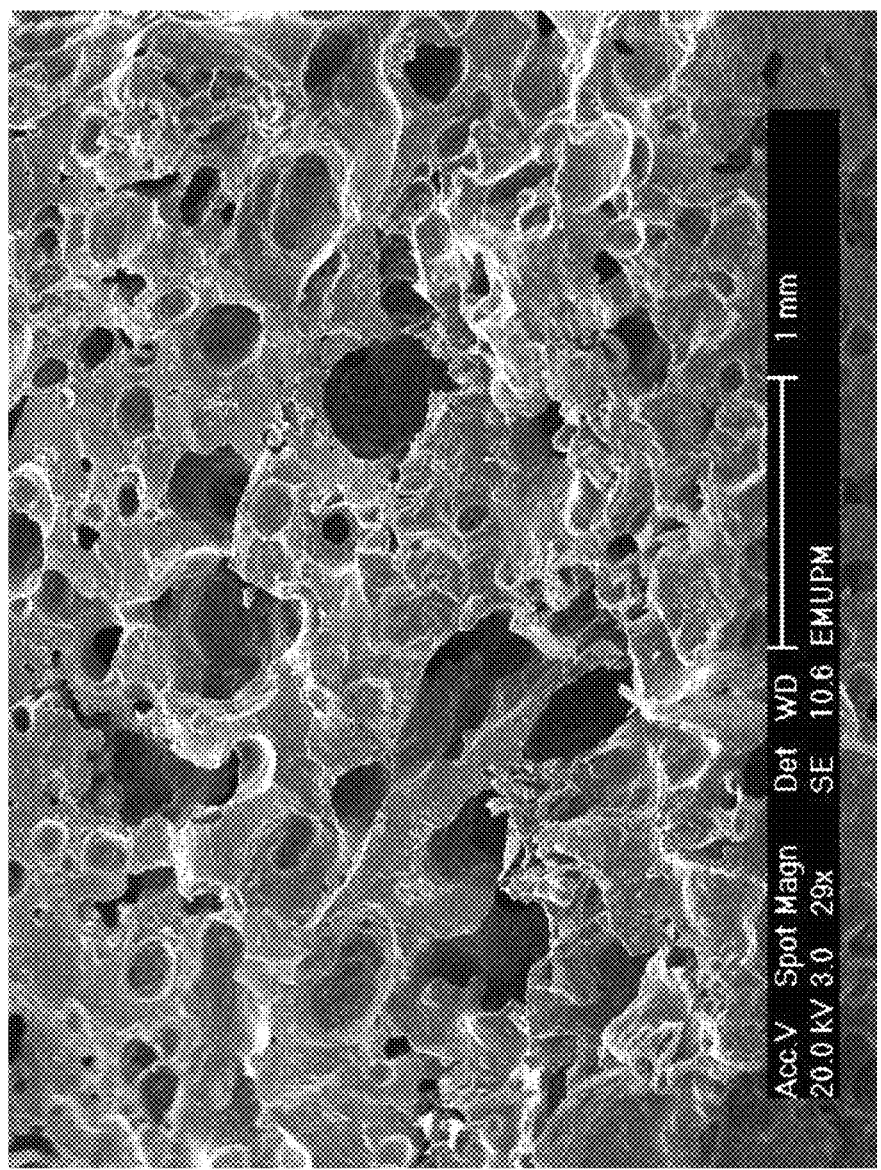
Figure 2D:
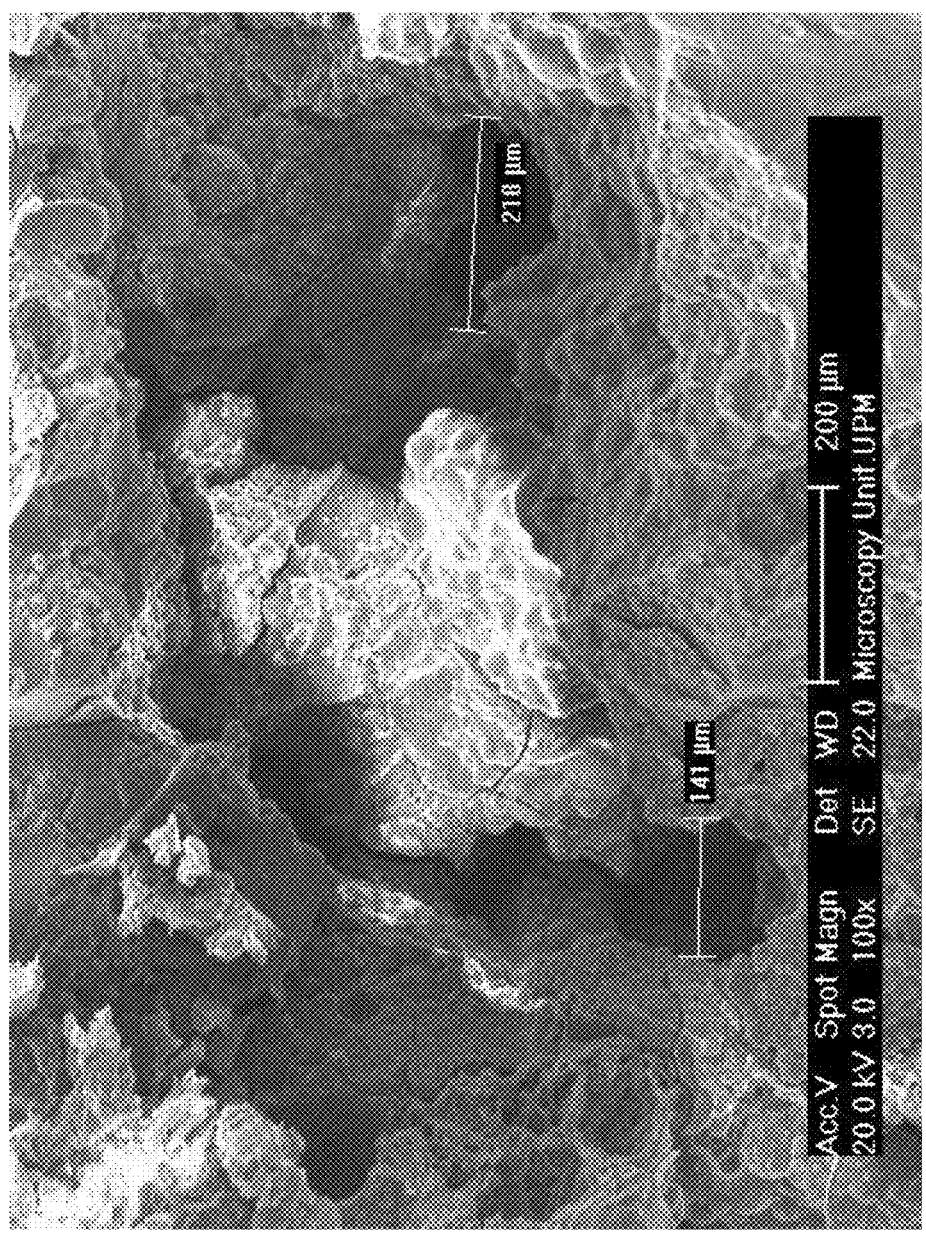
Figure 3A:
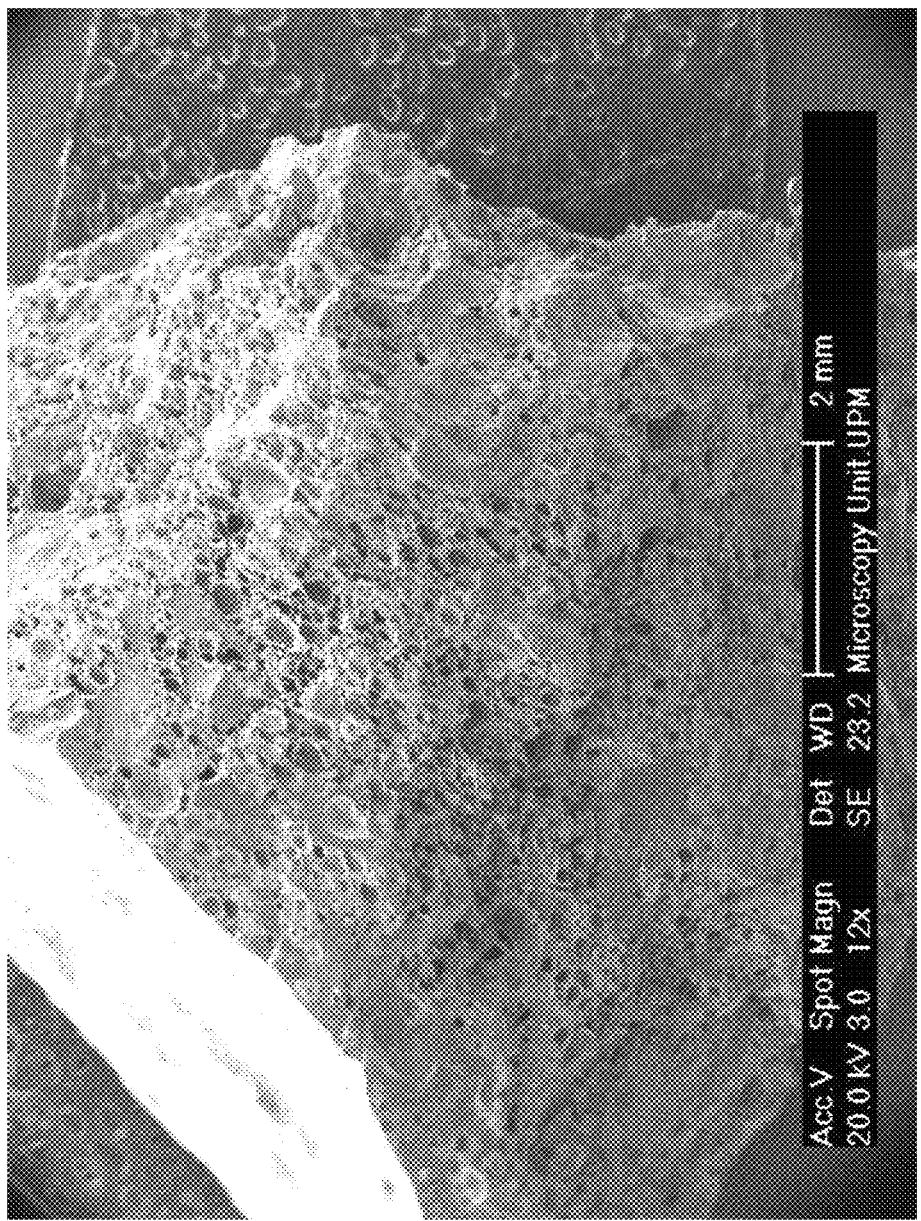
FIGS. 3A-D illustrates the scaffold contained of macro-micropores with different sizes and a uniform interior of sample 352 (the pore sizes are estimated between 20 to 400 nm).
Figure 3B:
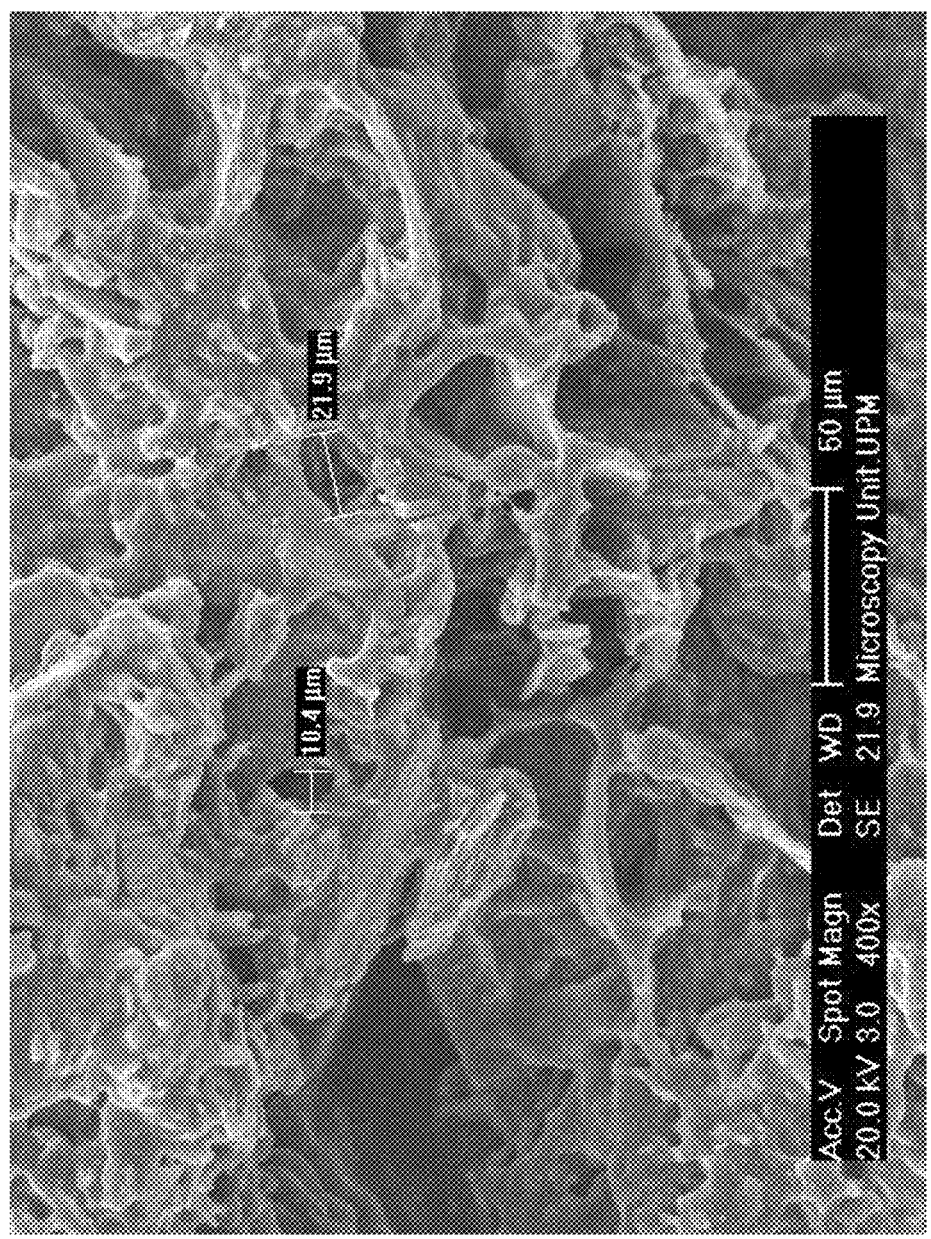
Figure 3C:
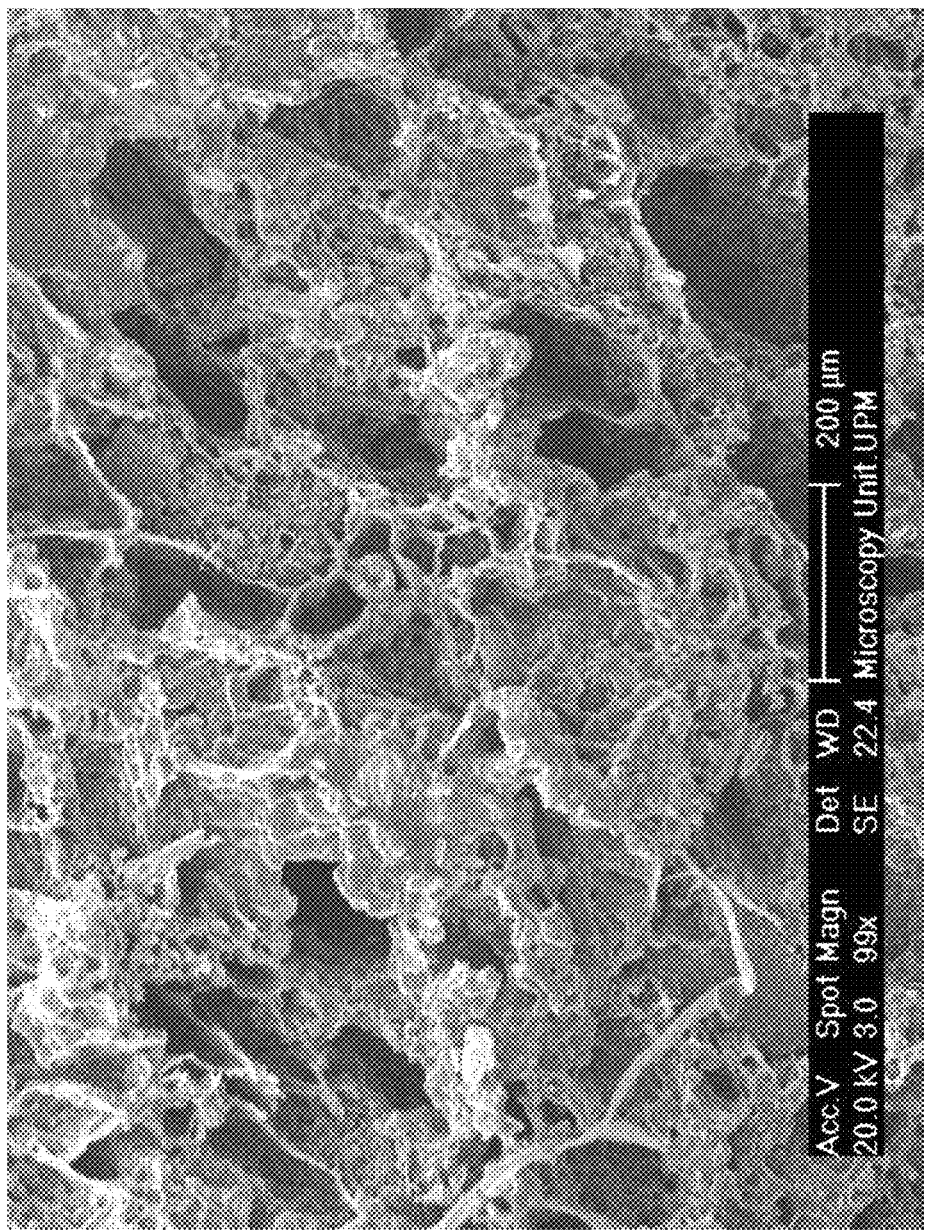
Figure 3D:
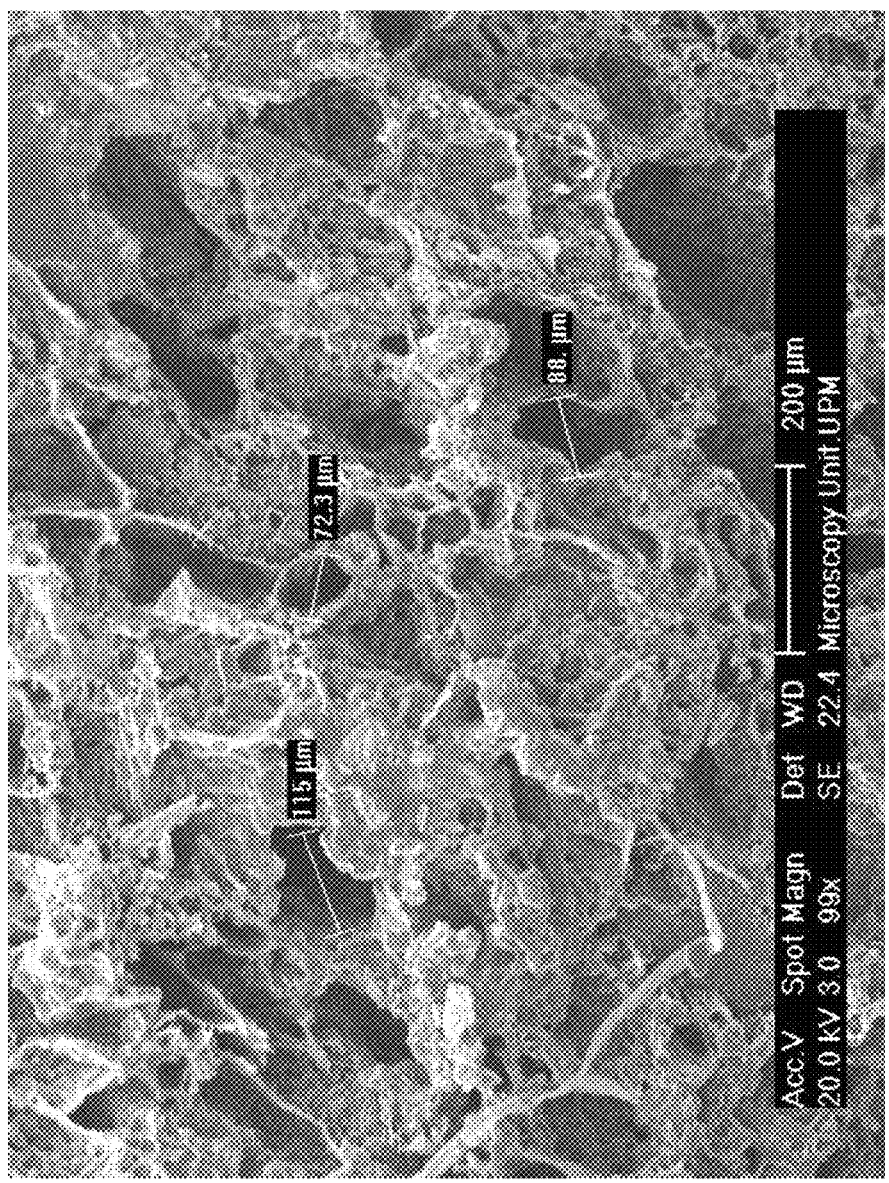
Figure 4A:
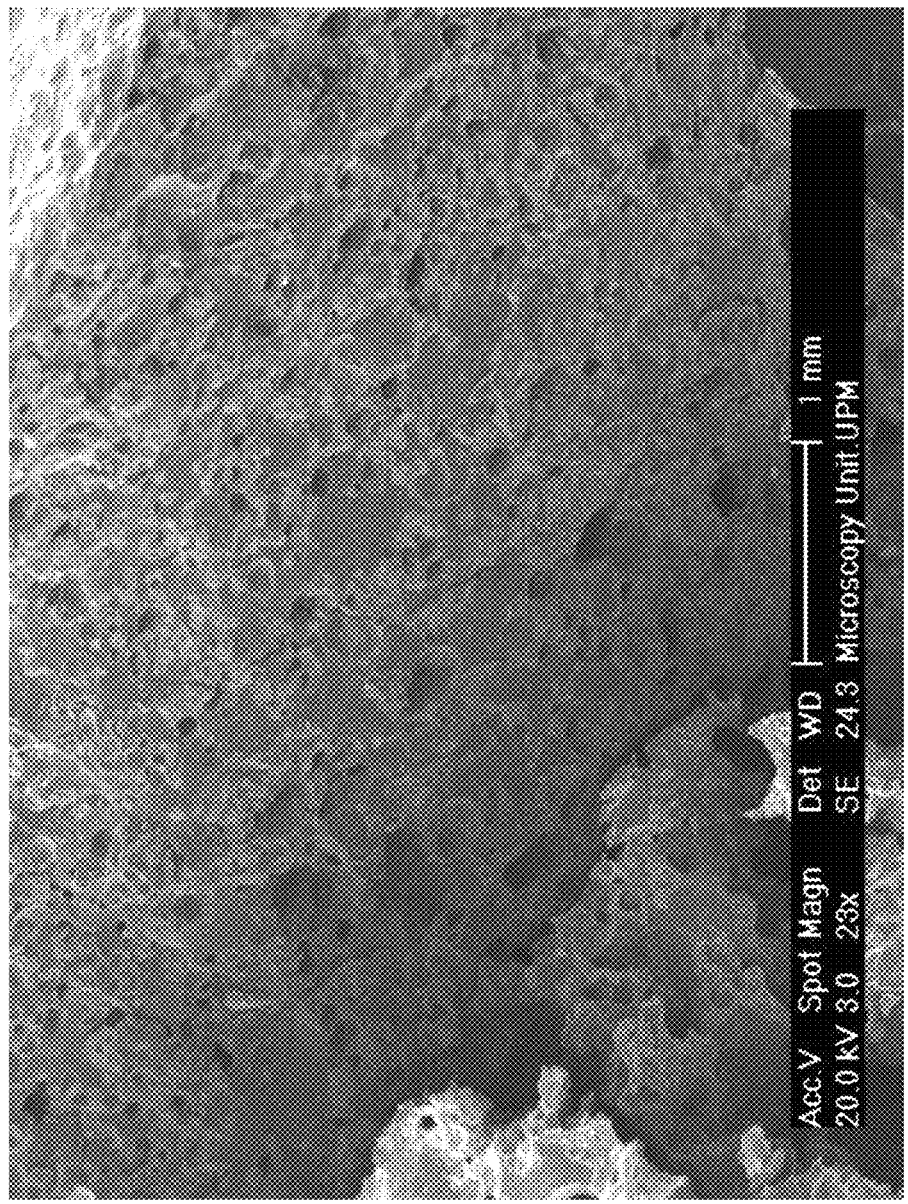
FIGS. 4A-B illustrates small diameter pores of sample 262 preferable to yield high surface area per volume.
Figure 4B:
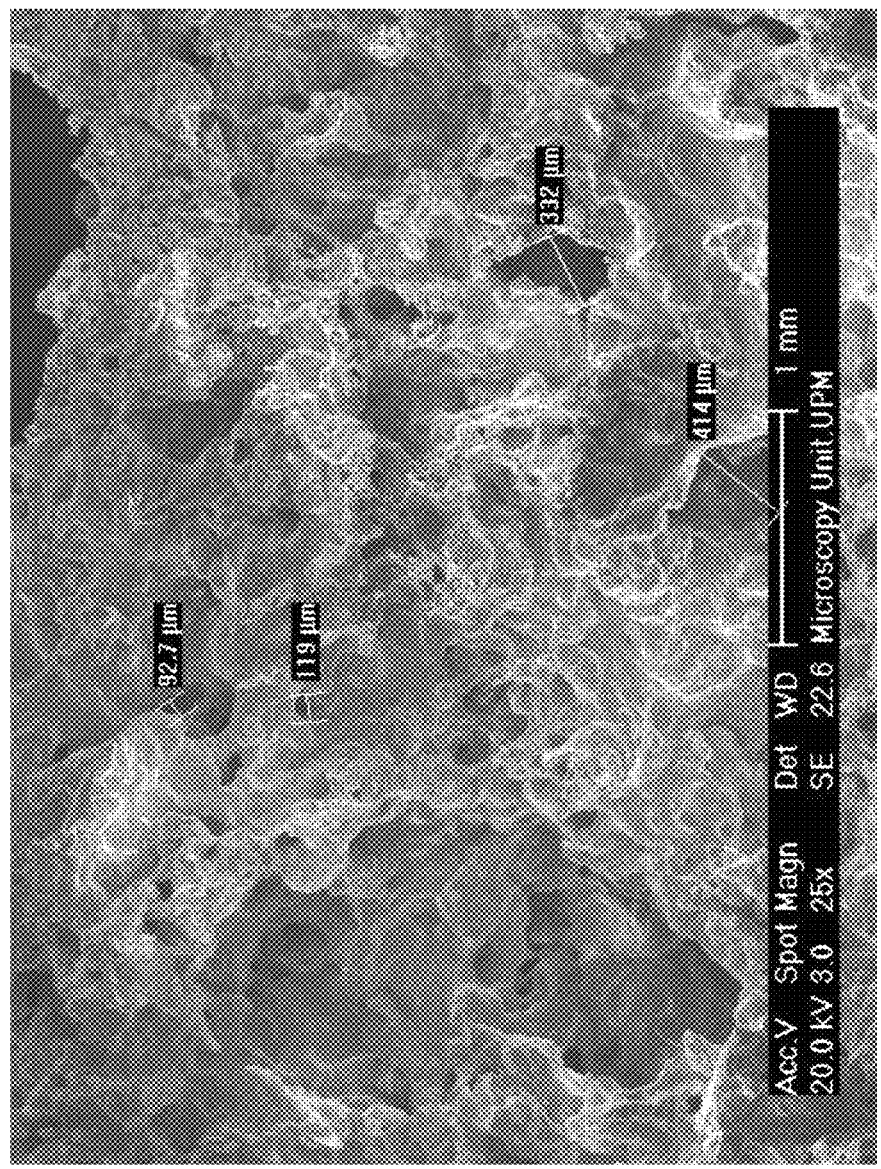
Figure 5A:
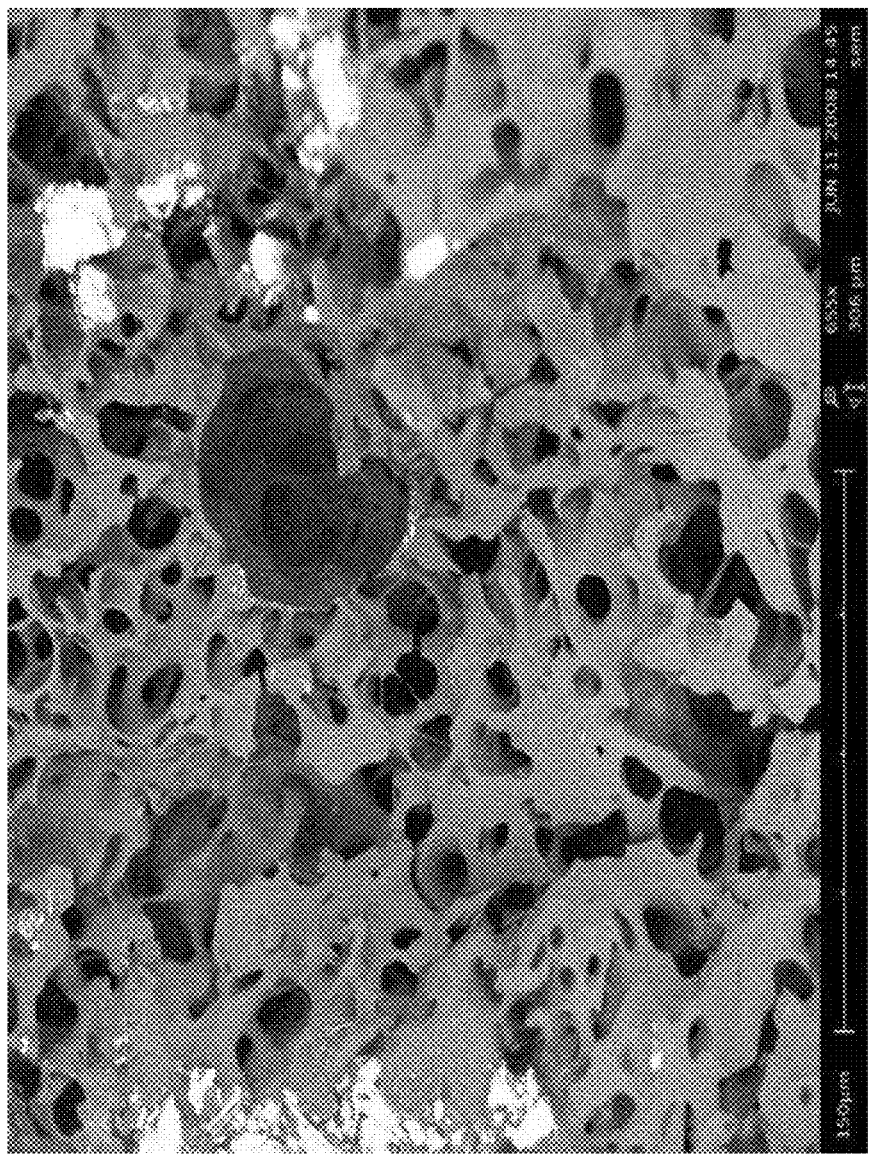
FIGS. 5A-D illustrates the porosity and interconnectivity of the pores (of scaffold prepared by the freeze-drying method) using the Phenom SEM.
Figure 5B:
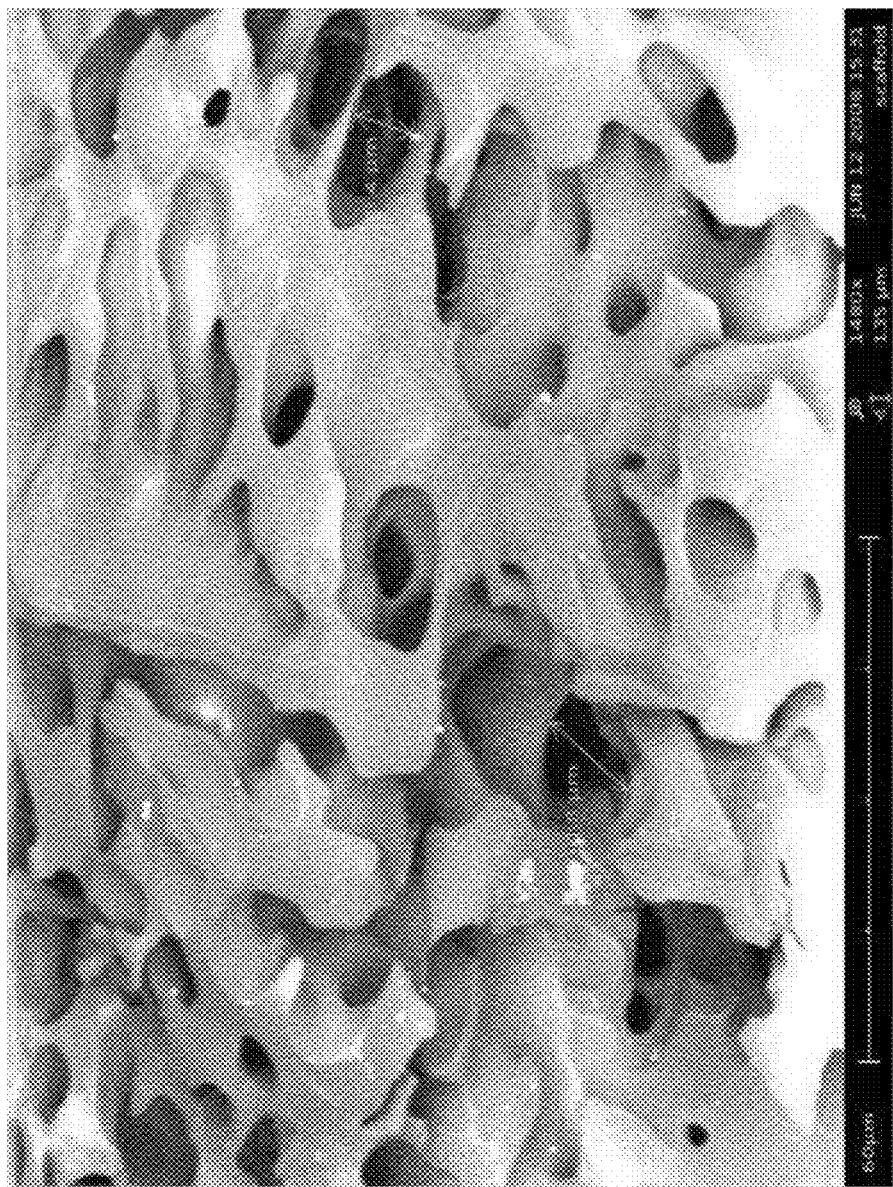
Figure 5C:
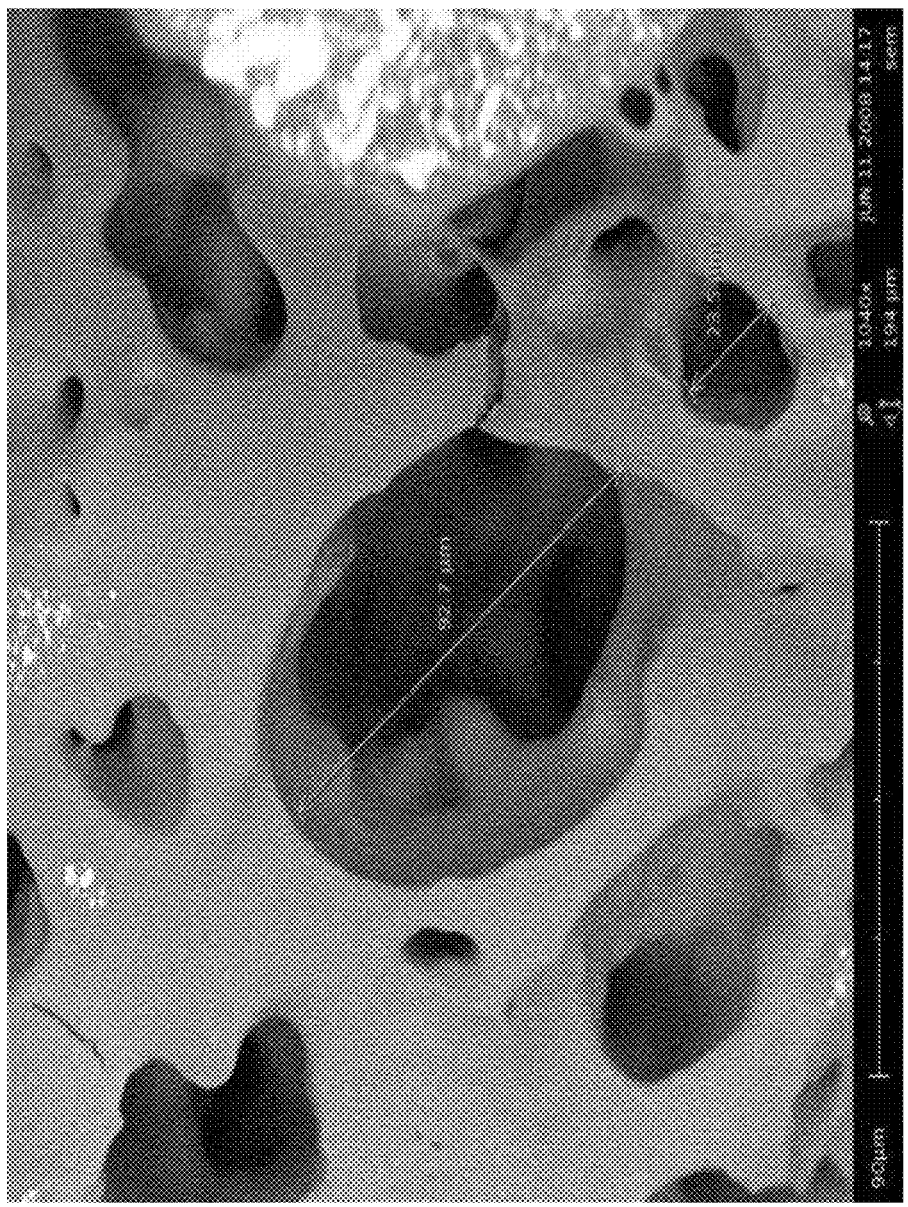
Figure 5D:

A more complete appreciation of the invention and many of the attendant advantages thereof can be better appreciated by reference to the following detailed description and the accompanying drawings. The following examples are cited by way of illustration and therefore, should not be construed to limit the scope of the present invention.

The present invention relates to a porous composition for bone scaffold. The porous composition comprises of a mixture of cockle shell powder, dextrin, gelatin and dextran. The cockle shell powder, the dextrin, the gelatin and the dextran are added at a certain amount respectively to form the mixture. Amount of the cockle shell powder is 33.33% by weight. Amount of the dextrin is ranging from 13.33% to 40% by weight. Amount of the gelatin is ranging from 13.33% to 20% by weight. Amount of the dextran is ranging from 13.33% to 40% by weight. A total mass of 150 g of the mixture is used as example where mass of the cockle shell is fixed at 50 g.

The present invention also relates to method for preparation of a porous composition for bone scaffold. In one embodiment, the method comprises of first, dissolving gelatin, dextran and dextrin in hot deionized water. Second, stirring the mixture. Third, adding cockle shell powder to the mixture. Fourth, pouring the mixture into a shaped wax block. Fifth, drying the mixture. Sixth, removing the shaped wax block and obtaining a scaffold and seventh, drying the scaffold.

In another embodiment, the method comprises of first, dissolving cockle shell powder, gelatin, dextran and dextrin in hot deionized water. Second, stirring the mixture. Third, pouring the mixture into a shaped wax block and fourth, drying the mixture in a freeze drying machine.

A more complete appreciation of the invention and many of the attendant advantages thereof can be better appreciated by reference to the following detailed description and the accompanying drawings. The following examples are cited by way of illustration and therefore, should not be construed to limit the scope of the present invention.

EXAMPLES

Materials for Scaffolds Preparation

Gelatin

Gelatin which is a natural protein derived from the organic phase of bone is much cheaper and more easily obtainable in solutions than collagen. It is needed to be dissolved in water and cross-linked to form a polymer network. The gelatin used was derived from bovine skin. Gelatin is used to enhance the paste, the firmness and rigidity of scaffold. The gelatin provides the mechanical strength by changes of chain of amino acids which occurred during heating or freeze-drying process.

Dextran

Dextran is a physiologically harmless biopolymer because of its biocompatible, biodegradable, non-immunogenic and non-antigenic properties. Dextran is used to increase the porosity of the scaffolds.

Dextrin

Dextrin is a simple carbohydrate with a low molecular weight. Dextrin is used widely in industry, due to their non-toxicity and their low price. Dextrin is tacky and has fast setting ability than common starch pastes formed by unmodified starch. After dissolving, it tends to setback and form gels which eventually become very firm and rigid.

Cockle Shell (*Anadara Granosa*) Powder

Cockles were collected from the wet markets and the powder was prepared after removal of all the waste material from the shells.

Scaffolds Preparation

Preparation of Cockle Shell Powder

This study introduces a novel three-dimensional biomatrix obtained from the Cockle (*Anadara granosa*) as a scaffold for tissue engineering. The powder from the shell was prepared according to the method described by Zuki et al. (2004), which involved the removal of all the waste material after boiling the shells for 30 minutes. The shells were thoroughly cleaned until the shells become completely white. The black line in shell junction border was also removed. The shells were subject to boiling again for a few minute to remove all the residual material and were dried in the oven at 40° C. over night. The cockle shells were ground by using warring blender (Blendor®, HCB 550, USA) until they turned into powder form. The powder was sieved at 90 µm by using stainless steel siever (Retsch, Germany) and sterilized by heat at 100° C. for few hours before ready to be used.

Preparation of the Scaffolds

Four-powder blend was formulated for the experiments. It consisted of cockle shell powder (50 g), gelatin (20 and 30 wt. %), dextran (20, 30, 40, 50 and 60 wt. %), dextrin (20, 40 and 60 wt. %).

Five different types of the scaffolds numbered 334, 352, 262, 226, 244 with various composition of gelatin, dextran, dextrin were prepared. The five scaffolds were prepared based on the following concentrations:

Scaffold 334: 50 g cs, 30 g gel, 30 g dextran, 40 g dextrin
Scaffold 352: 50 g cs, 30 g gel, 50 g dextran, 20 g dextrin
Scaffold 262: 50 g cs, 20 g gel, 60 g dextran, 20 g dextrin
Scaffold 226: 50 g cs, 20 g gel, 20 g dextran, 60 g dextrin
Scaffold 244: 50 g cs, 20 g gel, 40 g dextran, 40 g dextrin Keys cs=cockle shell
gel=gelatin Scaffolds Prepared by Heat Method The powders of three materials (gelatin, dextran, dextrin) were dissolved in hot deionized water at 70-80° C. for 2 hours by using the heating homogenize stirrer machines (Wiggen Hauser® Heating Stirring), the cockle shell powder was added to the mixtures in the end. The paste of the mixtures was poured in wax block design that depends on the shape of the bone defect, and left over night for drying at room temperature (27° C.). After 24 hours, the wax was removed and leaving the scaffolds to continue to dry at the same temperature for 1-2 days. Then, the scaffolds were dried in oven at 60° C. for 2 days. The scaffolds become hard and ready for sterilization to be used at a later date.

Scaffolds Prepared by Freeze-Drying Method

Four powders (cockle shell powder, gelatin, dextran, dextrin) were blended together with deionized water at 50° C. for 60 minutes by using stirrer machine to homogenize the materials. The paste was poured into the mold and transferred immediately into the deep freezer −80° C. for 24 hours. The block was removed and the scaffolds were dry by using freeze-dryer machines for 48 hrs at −50° C. The dry scaffolds were kept in clean place for sterilization.

Characterization of the Scaffolds

Environmental Scanning Electron Microscopy (ESEM)

Environmental Scanning Electron Microscopy (Philips XL30 ESEM) analysis revealed that the scaffold contained of macro-microspores with different sizes, and showed a uniform interior. The size of the pores and their distribution and also the interconnectivity between the pores were analyzed using the ESEM. Small diameter pores are preferable to yield high surface area per volume, as long as the pore size is greater than the diameter of a cell in suspension (typically 10 μm) (FIGS. 1-5).

Degradation Manner

The degradation manner of the scaffolds was assessed in water by soaking for 10 days. This was to evaluate the integrity of the scaffolds for few days in the liquid system. The scaffolds lasted for more than 10 days without much visible of the surface degradation. Qualitatively, the scaffolds were observed to be uniformly tough and strong throughout the test. The degradation rates should be adjustable to the suitable rate of tissue regeneration. After 10 days evaluation, the integrity of the scaffolds was still strong throughout the test.

Mechanical Tests

Compression test was conducted under the dry and wet condition of the scaffold with an Instron 4302 machine. Universal mechanical testing machine using 1-kN load cell (Canton). One sample of each type was tested. In each set, many samples of different size and shape was prepare but mostly like the bone except the compression used was rectangular produced of different geometries and dimensions as shown below in the Table 1. Stiffness of the different geometries and dimensions scaffolds were evaluated in the point stress region. The yield strength was taken at the yield point on stress-strain in MPa.

TABLE 1

The strength of the dry and wet scaffolds.

| NO | Sample | Width mm | Thickness mm | Yield strength MPa | Modulus MPa |
|---|---|---|---|---|---|
| 244 | Dry uninfiltrated | 14.30 | 7.97 | 11.43 | 144.5 |
| 244 | Dry infiltrated | 13.74 | 7.04 | 13.95 | 182.3 |
| 244 | Wet infiltrated | 13.96 | 8.50 | 1.946 | 0.696 |
| 262 | Dry uninfiltrated | 15.63 | 7.64 | 3.628 | 74.57 |
| 262 | Dry infiltrated | 16.32 | 8.37 | 3.429 | 20.74 |
| 262 | Wet infiltrated | 13.56 | 8.87 | 0.132 | 0.428 |
| 352 | Dry uninfiltrated | 12.60 | 7.49 | 13.19 | 187.5 |
| 352 | Dry infiltrated | 15.91 | 9.93 | 9.676 | 71.41 |
| 352 | Wet infiltrated | 16.78 | 11.15 | 0.394 | 0.751 |
| 334 | Dry uninfiltrated | 29.4 | 2.66 | 7.271 | 1231 |
| 334 | Dry infiltrated | 29.13 | 2.92 | 5.801 | 33.24 |
| 334 | Wet infiltrated | 29.10 | 4.49 | 0.007 | 4.077 |
| 226 | Dry uninfiltrated | 15.38 | 9.78 | 4.894 | 48.05 |
| 226 | Dry infiltrated | 13.89 | 7.80 | 5.250 | 148.8 |
| 226 | Wet infiltrated | 15.75 | 9.57 | 2.779 | 0.639 |

Differential Scanning Calorimetry (DSC)

Different ratio of scaffolds samples were analyzed on differential scanning calorimetry (DSC). The thermal transition of powder was analyzed by using METTLER TOLEDO (DSC822$^e$ Switzerland). Typically, 5 mg of three samples were weighed. They were scanned from room temperature (25° C.) up to 250° C. at the rate of 10° C./min.

Figure 6A:
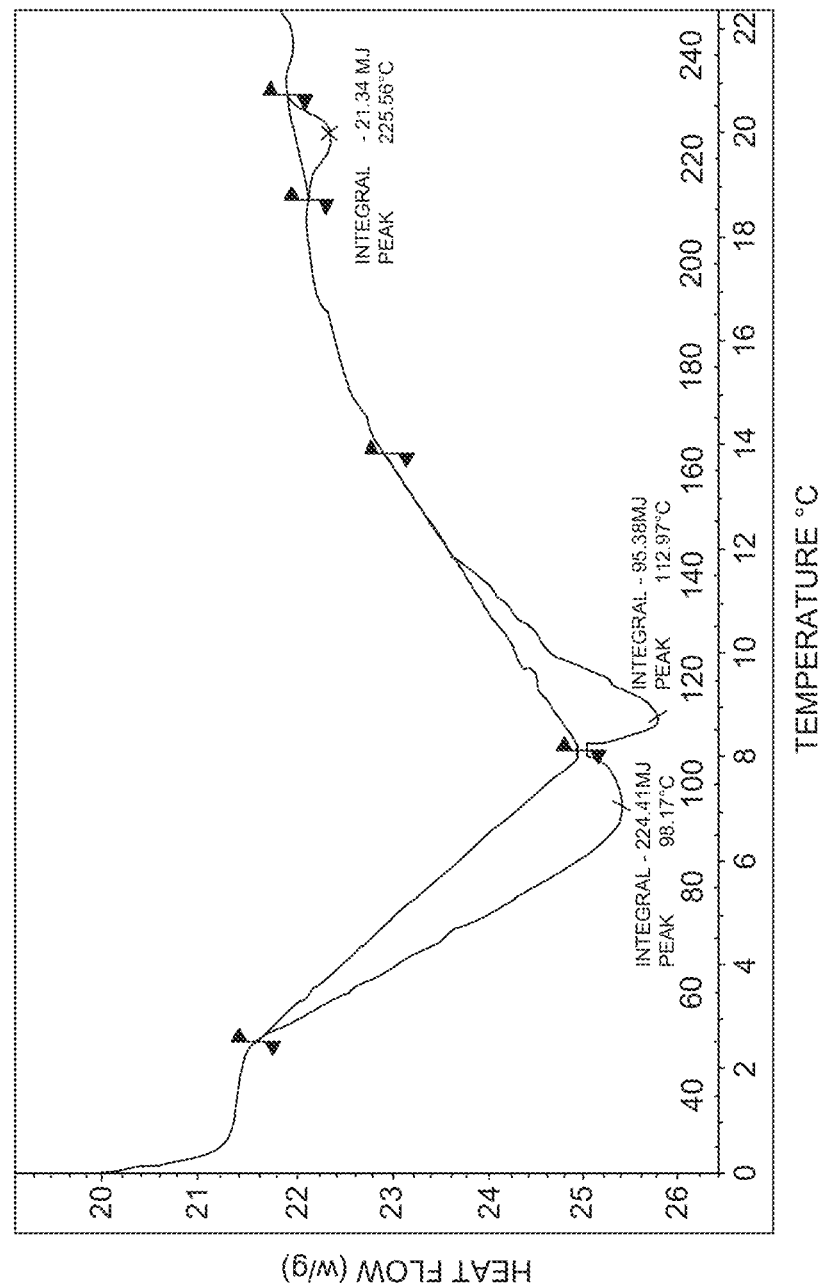
FIGS. 6A-B illustrate DSC-temp. vs. heat flow for two sample, sample 262 and 334.
Figure 6B:
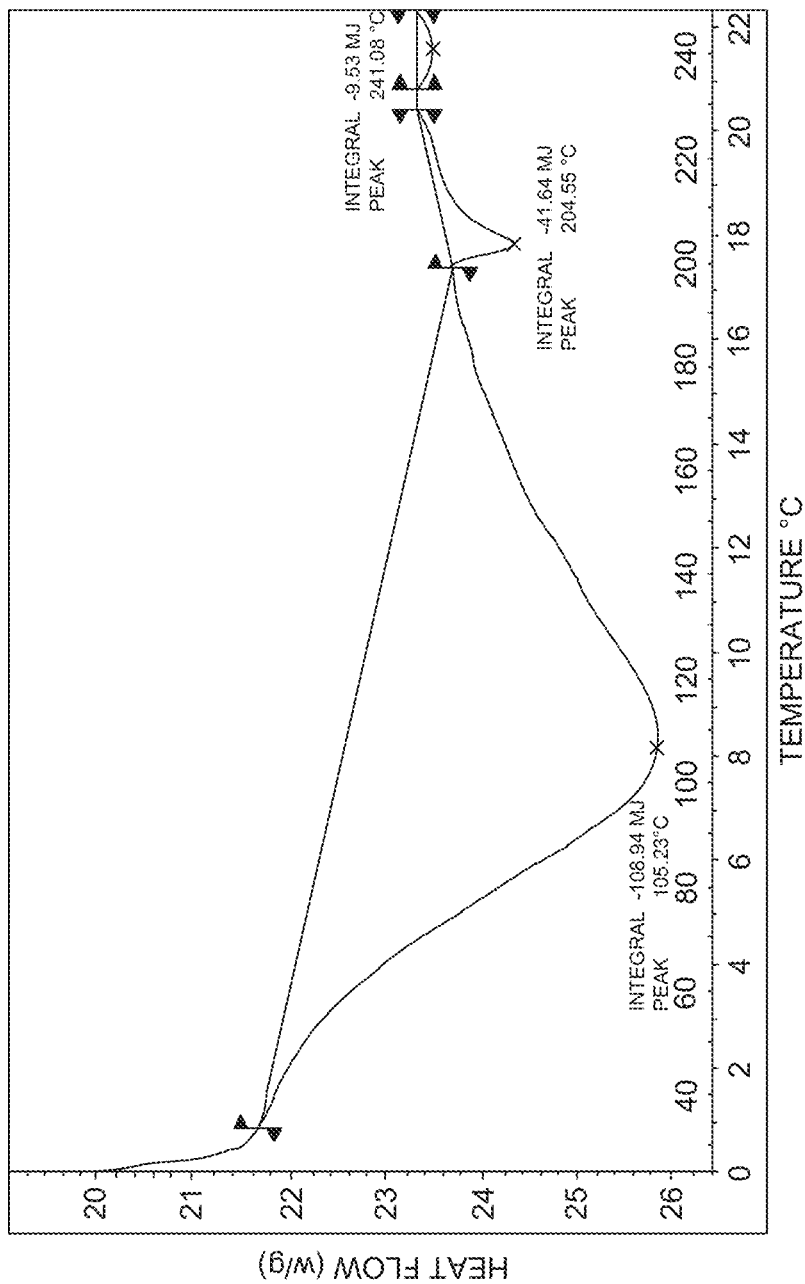
Figure 7A:
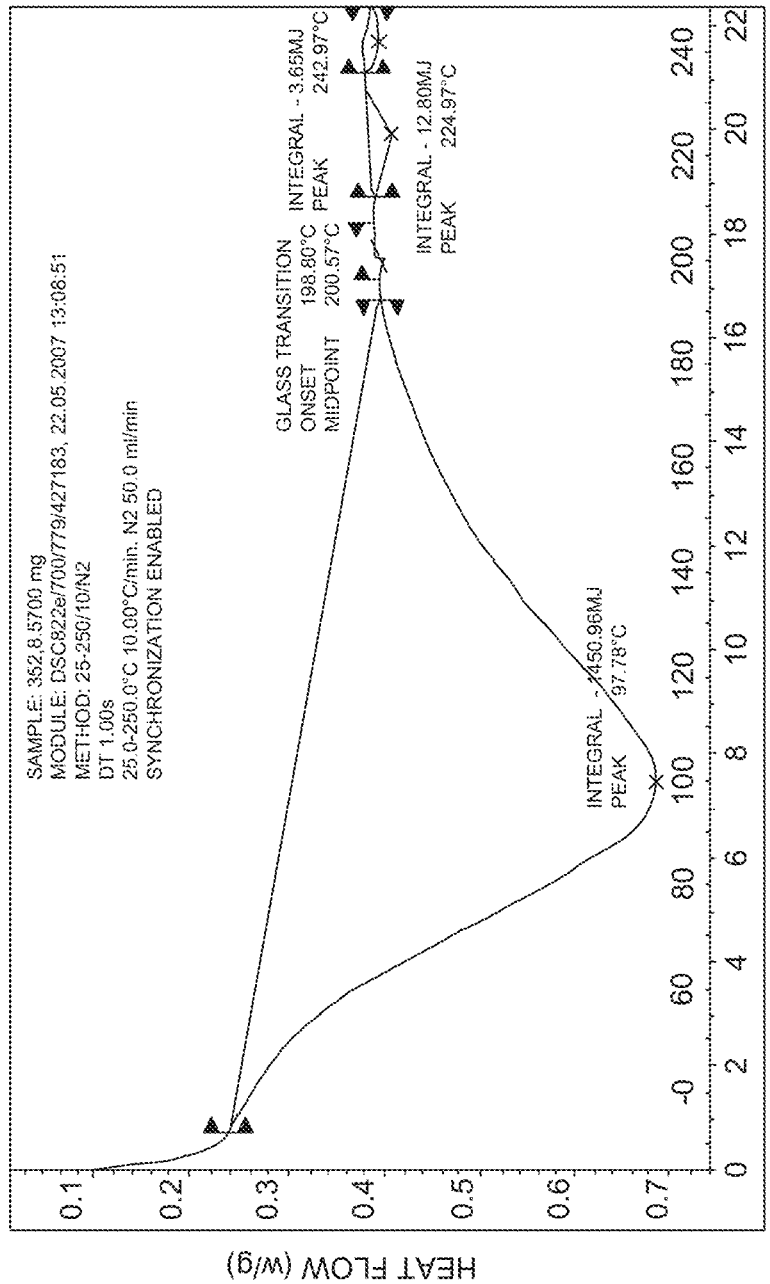
FIGS. 7A-B illustrate DSC-temp. vs. heat flow for one sample, sample 352.
Figure 7B:
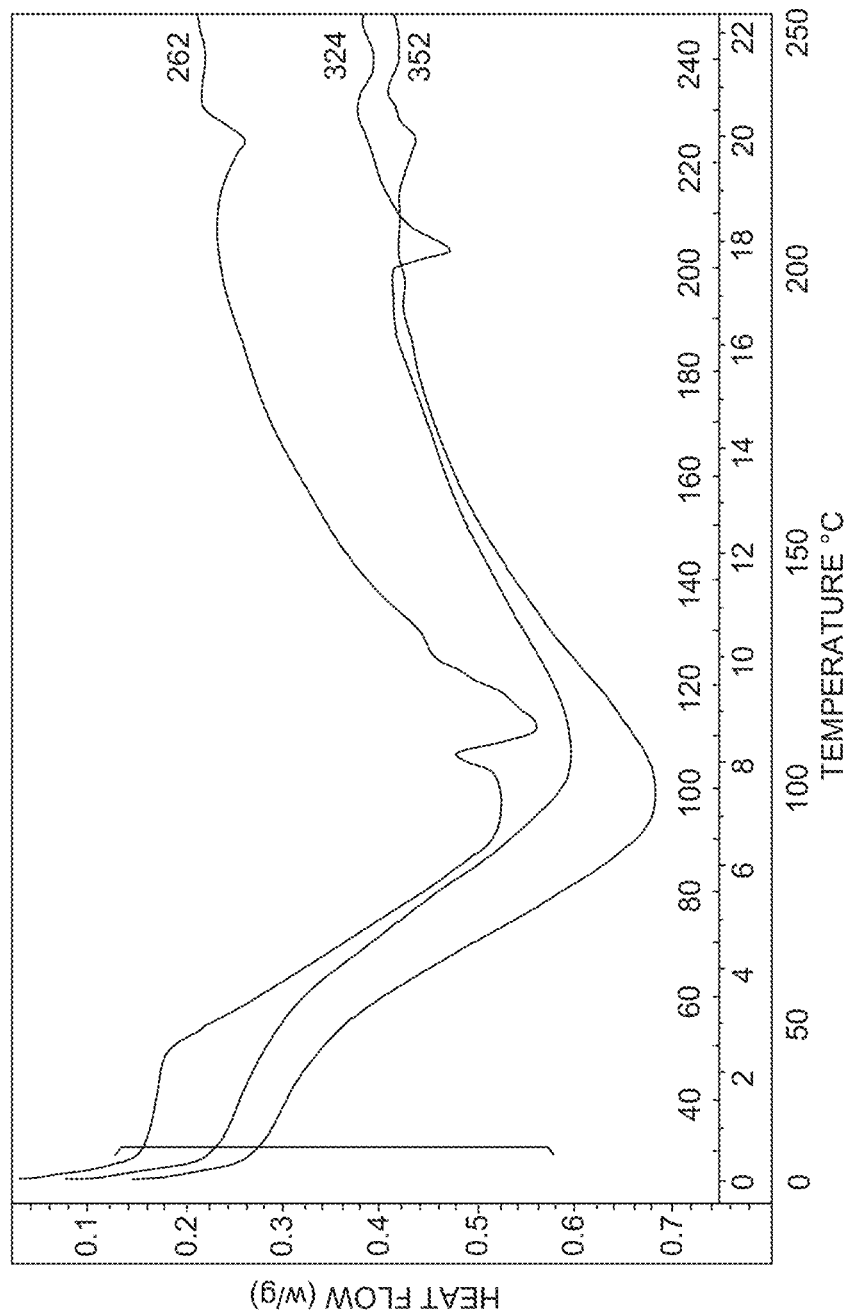

DSC was used to analyze the thermal transition of the powders that used to fabricate scaffolds. The second peak observed could be ascribed to the melting of crystallites of the cockle shell powder, the first peaks of the sample observed refer to the three powders. The thermal signature was that of the scaffolds with a first peak 100° C. and second peak of sample. It also showed good mix ability between the materials in forming new bonds (FIGS. 6-7).

X-Ray Diffraction Analysis

Examination of wide-angle X-ray diffraction was performed at room temperature to characterize the crystalline amorphous nature and identifies any crystalline phases present. Utilize the diffractometer system X'PERT.PRO Philips PW3040/60 (XRD) with the diffraction angles from 0-70°. The scaffolds were ground before the analysis. 40 kV acceleration voltage and 30 mA were used for analysis.

Figure 8:
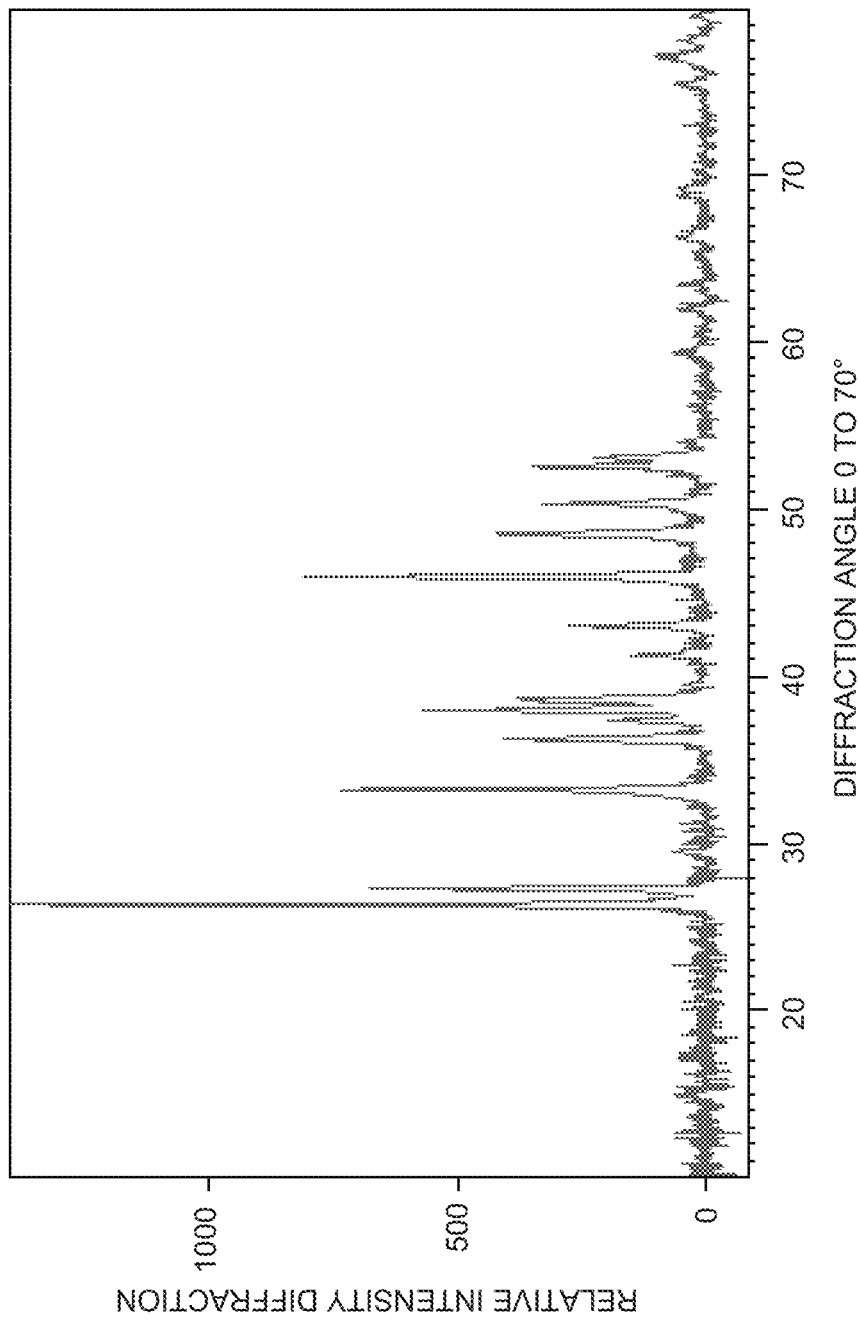
FIG. 8 illustrates a typical XRD pattern of the products (sample 352).
Figure 9:
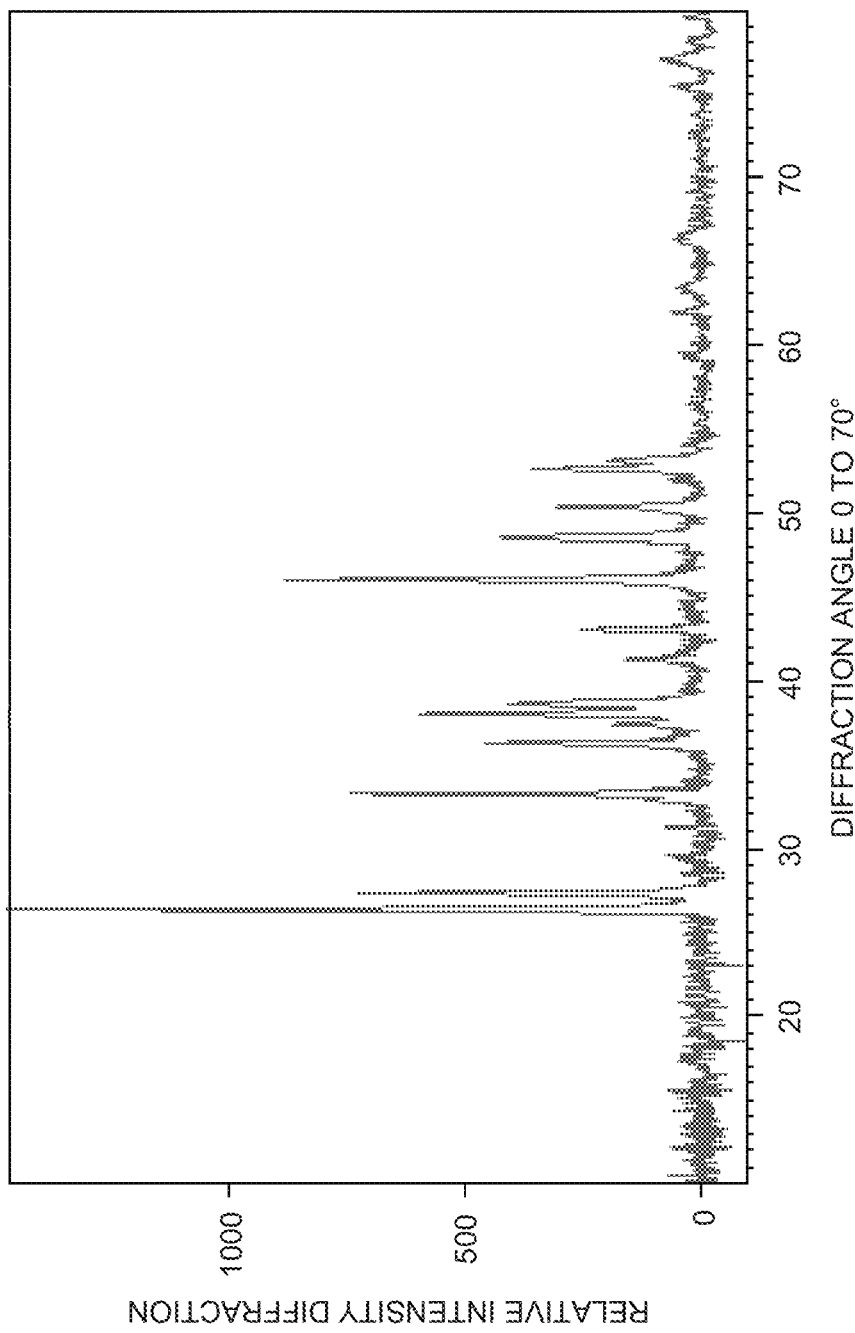
FIG. 9 illustrates a typical XRD pattern of the products (sample 262).

XRD was used to characterize the crystalline/amorphous nature of the $CaCO_3$ and to identify any crystalline phases present. Only the major $CaCO_3$ reflection peak, such as more than 1000 and between the 500 and 1000 were present in the X-ray diffraction pattern of these nano$CaCO_3$ particles, no common secondary phase, such as gelatin, dextrin, dextran were found, which confirmed the phase composition of $CaCO_3$ (FIGS. 8-9).

Water Absorption Test

The samples were infiltrated with different amounts of copolymer solution, which was made by poly (L-lactide) PLA and polycaprolactone PCL dissolving in dichloromethane ($CH_2Cl_2$) non toxic solution and highly vaporized. Different types of scaffolds were soaked in water for 10 minutes and evaluated the amount of water absorbed. The second 10 minutes of soaking was conducted after the scaffolds were soaked in water for 10 minutes and dried.

The scaffolds were soaked in water for 10 minutes and evaluated for the amount of water absorbed by the freezing method.

Figure 10:
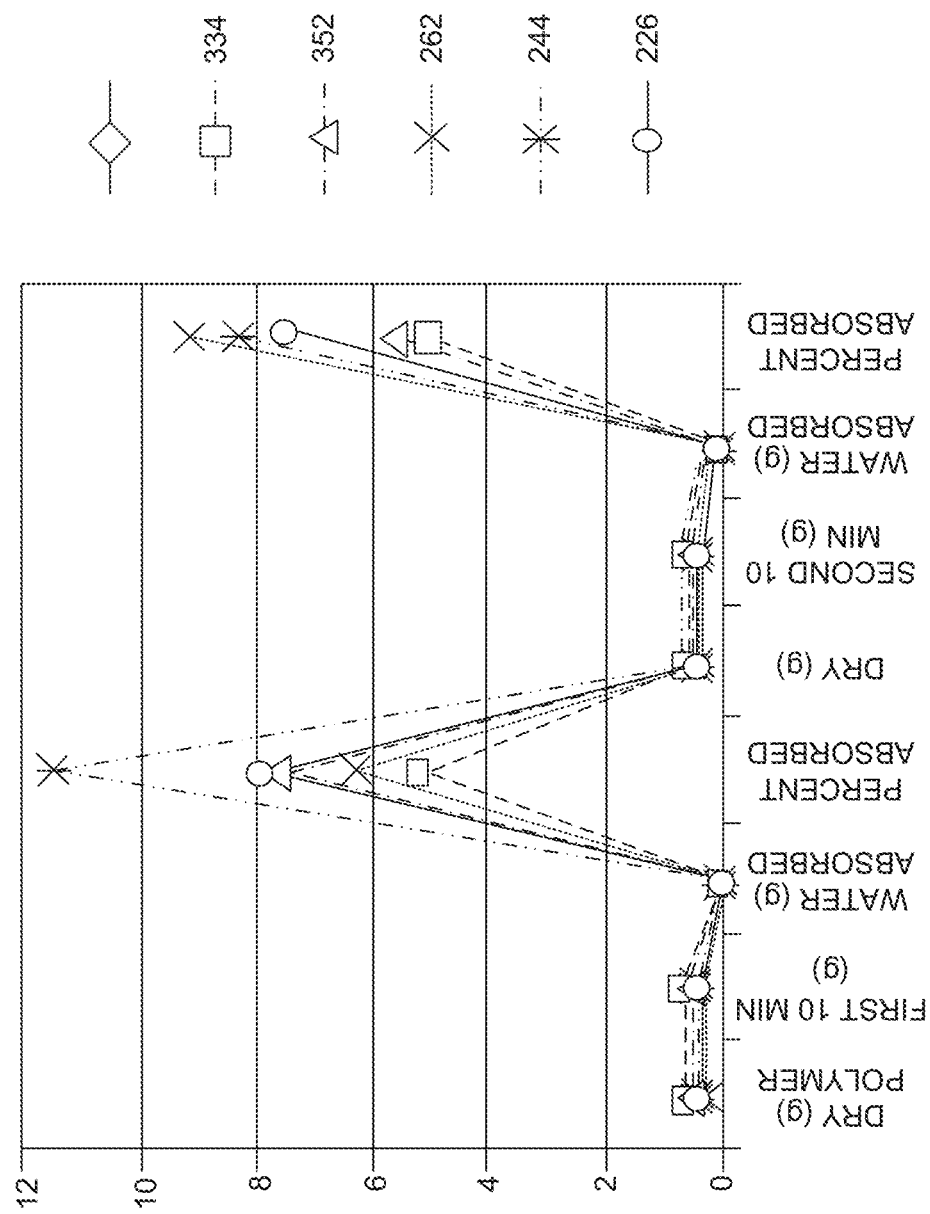
FIG. 10 illustrates a graph showing the amount of water absorbed in all samples.

The results in FIG. 10 reveals that, as the volume of the copolymer used gets larger, the resistance to water absorption becomes better. After the first 10 minutes, the sequence infiltrated scaffolds in group 244 (11.428), 352 (7.547) were more resistant than those infiltrated by group 334 (5.172), 226 (7.692), 262 (6.25).

The invention being thus described, it will be apparent that the same may be varied in many ways. Such variations are to be regarded as within the scope of the invention, and all such modifications as would be apparent to one skilled in the art are intended to be within the scope of the following claims.

The invention claimed is:

1. A method for preparation of a porous composition for 3D-scaffolds comprising the steps of:
(a) dissolving gelatin, dextran and dextrin in hot deionized water,
(b) stirring the mixture,
(c) adding cockle shell powder to the mixture,
(d) pouring the mixture into a shaped wax block,
(e) drying the mixture,
(f) removing the shaped wax block and obtaining a scaffold,
(g) drying the scaffold.

2. The method of claim 1, characterized in that prior to adding the cockle shell powder at step (c), the cockle shell powder is sieved at 90 μm.

3. The method of claim 1 characterized in that in step (a) the hot deionized water is at temperature of 70-80° C. and the step (a) is performed for 2 hours.

4. The method of claim 1 characterized in that in step (d) the shaped and the size of wax block is design depending on the shape and the size of the bone defect.

5. The method of claim 1 characterized in that step (e) is achieved by leaving the mixture over night at room temperature and pressure.

6. The method of claim 1 characterized in that step (f) the scaffold is dried at room temperature for 1 or 2 days then, the scaffold is dried in an oven at 60° C. for 2 days.

7. A method for preparation of a porous composition for 3D-scaffolds comprising the steps of:
   (a) dissolving cockle shell powder, gelatin, dextran and dextrin in hot deionized water,
   (b) stirring the mixture,
   (c) pouring the mixture into a shaped wax block,
   (d) drying the mixture in a freeze drying machine.

8. The method of claim 7, characterized in that the cockle shell powder at step (a) is sieved at 90 μm.

9. The method of claim 7 characterized in that in step (a) the temperature of hot deionized water is at 60° C.

10. The method of claim 7 characterized in that in step (b) the step is perform for 60 minutes in stirrer machine to homogenized the materials.

11. The method of claim 7 characterized in the in step (d) the temperature of the deep freezer −80° C.

12. The method of claim 7 characterized in that step (d) is performed for 24 hours.

13. The method of claim 7 characterized in that the scaffold is further dried by using freeze-dryer machines for 24 hours at −50° C.

* * * * *